United States Patent
Busacca et al.

(10) Patent No.: US 7,994,335 B2
(45) Date of Patent: Aug. 9, 2011

(54) ELECTRONICALLY TUNED LIGANDS FOR ASYMMETRIC HYDROGENATION

(75) Inventors: Carl Alan Busacca, Poughkeepsie, NY (US); Jon Charles Lorenz, New Milford, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 12/514,319

(22) PCT Filed: Nov. 20, 2007

(86) PCT No.: PCT/US2007/085165
§ 371 (c)(1),
(2), (4) Date: May 11, 2009

(87) PCT Pub. No.: WO2008/067218
PCT Pub. Date: Jun. 5, 2008

(65) Prior Publication Data
US 2010/0041898 A1 Feb. 18, 2010

Related U.S. Application Data

(60) Provisional application No. 60/867,419, filed on Nov. 28, 2006.

(51) Int. Cl.
*C07F 9/28* (2006.01)
*C07F 9/547* (2006.01)

(52) U.S. Cl. ........................................ 548/113; 548/119
(58) Field of Classification Search ............... 548/354.1; 514/401
See application file for complete search history.

(56) References Cited

U.S. PATENT DOCUMENTS 6,316,620 B1 11/2001 Busacca

OTHER PUBLICATIONS

Busacca et al, Journal of Organic Chemistry (2004), vol. 69 (16), pp. 5187-5195.*
Allen et al. J. Chem. Soc., Perkin Trans. 1, 1998, pp. 335-340.*
Busacca et al., Organic Letters (2009) 11(24), 5594-5597.*
International Search Report for PCT/US2007/085165 mailed Mar. 3, 2008.
Blaser, H-U., et al, "Solvias Josiphos ligands: from discovery to technical applications." Topics in Catalysis, vol. 19, No. 1, Mar. 2002, pp. 3-6.
Burk, J. J. "The DuPHOS Ligands-A Historical Account". Chemtracts, Organic Chemistry, Nov. 1998 (11), 787-802.
Jacobsen, E.N. Pflatz, A, Yammamaoto, H, Eds. "Comprehensive Asymmetric Catalysis" vol. 1, pp. 121-182, Springer-Verlag, 1999.
Knowles, W.S., et al, "Asymmetric Hyrdogentations (Nobel Lecture)". Angew. Chem, Int. Ed., 2002, 41 (12), pp. 1998.
Kumobayaski, H., et al, "Recent Advances of BINAP Chemistry in the Industrial Aspects" Synlett 2001, pp. 1055-1064.
Liu, D., et al, "A new class of readily available and conformationally rigid phosphio-oxazoline ligands for asymmetric catalysis" XP-002469285. Tetrahedron 61, 2005, pp. 6450-6471.
Menges, F., et al "Synthesis and application of chiral phosphino-imidazoline ligands: Ir-catalyzed enantioselective hydrogenation" XP-002469286. Organic Letters, 2002, vol. 4, No. 26, pp. 4713-1716.
Noyori, R. "Catalytic Hydrogenation: A Core Technology in Synthesis" Adv. Synth. Catal. , 2003, No. 1&2, pp. 345.
Tang, W., et al, "New Chiral Phosphorus Ligands for Enantioselective Hydrogenation" Chem. Rev, 2003, 103, pp. 3029-3069.

* cited by examiner

*Primary Examiner* — Kamal Saeed
*Assistant Examiner* — Nyeemah A Grazier
(74) *Attorney, Agent, or Firm* — Michael P. Morris; Usha R. Patel; Anthony P. Bottino

(57) ABSTRACT

Disclosed is a new class of chiral bidentate ligands capable of performing asymmetric hydrogenation. Also disclosed are processes of performing asymmetric hydrogenation the chiral bidentate ligands.

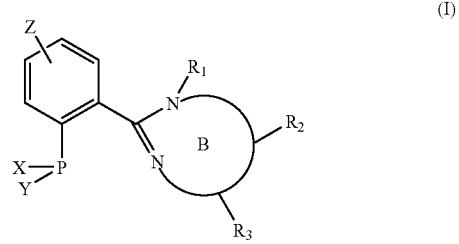

4 Claims, No Drawings

ELECTRONICALLY TUNED LIGANDS FOR ASYMMETRIC HYDROGENATION

This application is a 371 National Stage filing of PCT/US2007/085165 filed on Nov. 20, 2007. This application also claims benefit to U.S. provisional application Ser. No. 60/867,419 dated Nov. 28, 2006.

BACKGROUND OF THE INVENTION

Asymmetric synthesis has become increasingly important in the pharmaceutical industry. There is growing regulatory pressure to approve only those enantiomers of drugs that have the desired biological activity. For safety reasons and to demonstrate efficacy, regulatory agencies are taking the position that only those enantiomers with pharmaceutical action should be administered, apart from the enantiomers with little or no action or even adverse or toxic effect. The total market for enantiomerically pure pharmaceuticals is close to ninety billion U.S. dollars. To prepare large quantities of drugs via classical resolution is often cost prohibitive, and such drugs will commonly be prepared via asymmetric synthesis.

Many asymmetric syntheses involve the use of catalysts, and typically employ chiral ligands and late transition metals. Asymmetric hydrogenation is a synthetic transformation that has been used industrially on large scale (see *Asymmetric Catalysis on Industrial Scale*, H. U. Blaser and E. Schmidt, Eds., Wiley-VCH, 2004), usually utilizing so-called "functionalized olefins", that is, olefins that contain some additional close functionality, such as unsaturated esters, enamides, enecarbamates, and dehydroaminoester and dehydroaminoacid derivatives. These are discussed in a good recent review on the topic (*Comprehensive Asymmetric Catalysis*, Vol. 1, pp. 121-182, E. N. Jacobsen, A. Pfaltz, H. Yamamoto, Eds., Springer-Verlag, 1999).

Some of the most successful commercial ligands for this type of asymmetric hydrogenation are 1) The DuPhos family of ligands (for a review, see: Burk, M. J. *Chemtracts* 1998, 11(11), 787.) 2) The Zhang ligands such as TangPhos and DuanPhos (Zhang, X.; Tang, W. Chemical Reviews 2003, 103(8), 3029. 3) The Josiphos family of ligands from Solvias (for a review, see: Blaser, H.-U. et al *Topics in Catalysis* 2002, 19(1), 3.) 4) BINAP and it's derivatives (for reviews, see: a) Noyori, R.; *Adv. Syn. Catalysis* 2003, 345 (1+2), 15. b) Saito, T. et al, *Synlett* 2001, 1055) and 5) Dipamp (for a review, see: Knowles, W. S., *Angew. Chem. Int. Ed.* 2002, 41(12), 1998.).

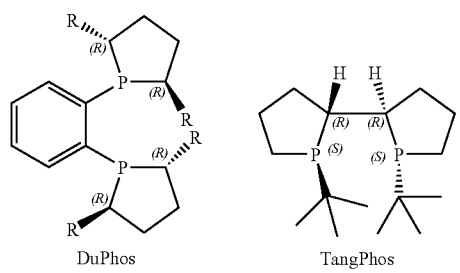

DuPhos                    TangPhos

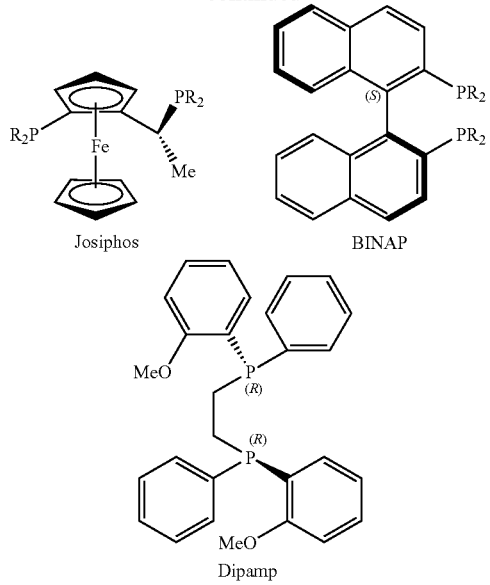

Josiphos                   BINAP

Dipamp

Bidentate ligands play a central role in catalyst design for asymmetric synthesis, because they can hold the metal in a relatively rigid and defined spatial environment. Almost all successful ligands for asymmetric hydrogenation are of the "P-P" type, that is, the metal atom binds to two phosphorus atoms. For the P-P ligands in the literature, the most common metals used are rhodium, iridium, and ruthenium, with rhodium being most commonly employed and often preferred.

U.S. Pat. No. 6,316,620 discloses a class of electronically-tunable chiral ligands (BIPI Ligands) of the "P-N" type (1). A typical example is shown below. This ligand platform has an advantage over the systems just named: it's electronic properties can be

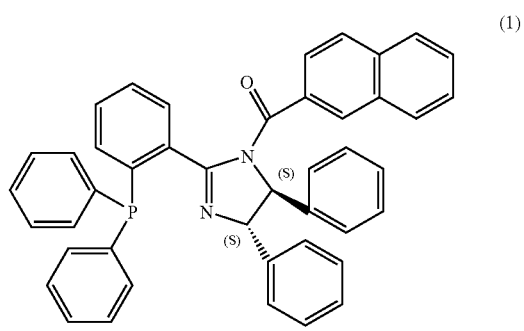

(1)

dramatically altered just by changing the substituent on the imidazoline nitrogen atom. If this N-substituent is an alkyl group, for example, the ligand will be basic and a "strong" donor, while an acyl N-substituent, for example, will lead to a neutral ligand that is a weaker donor. These electronic properties can therefore be "tuned" for different types of asymmetric transformations as needed. We have demonstrated the successful use of this electronic tuning concept in the asymmetric Heck Reaction ((a) C. Busacca et al, *Org. Lett.* 2003, 5(4), 595. b) C. Busacca, et al *J. Org. Chem.* 2004, 69(16), 5187.)), and Pfaltz has shown the use of the BIPI Ligands (*Org. Lett.* 2002, 4(26), 4713) for asymmetric hydrogenation of unfunctionalized olefins.

There is interest in the use of electronically tunable chiral ligands for the asymmetric hydrogenation of dehydrourea esters, such as 1 below. Asymmetric hydrogenation of this class of olefins does not appear to have been studied previously. As shown in Scheme 1a, the product 3 is formed after the initial adduct 2, is further hydrogenated to reduce the terminal olefin. The chirality-inducing event is the first step.

Scheme 1a

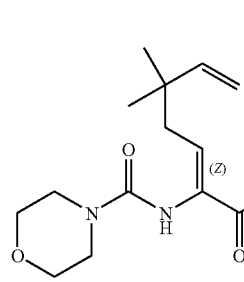

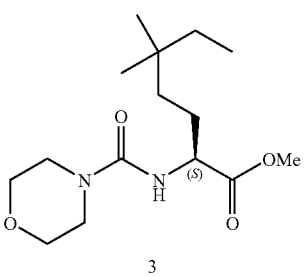

SUMMARY OF THE INVENTION

It is therefore an object of the invention to provide a new class of chiral bidentate ligands as described herein-below capable of performing asymmetric hydrogenation.

It is another object of the invention to provide a process of performing asymmetric hydrogenation for compounds found in U.S. Pat. No. 6,420,364 and US Publication No. 2004-0180886 A1, such as but not limited to (1) shown herein above in Scheme 1b.

Scheme 1b

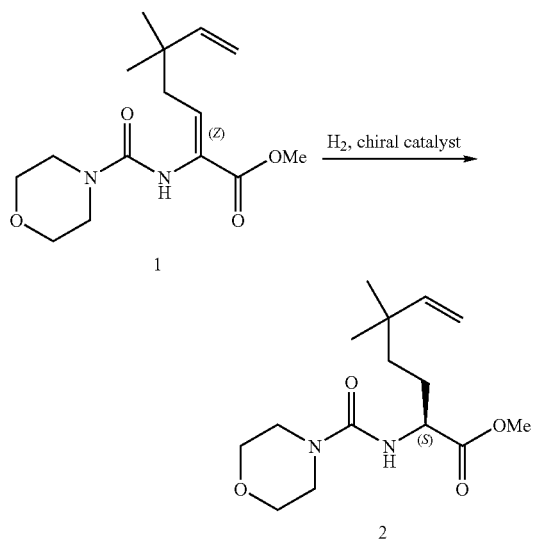

DETAILED DESCRIPTION OF THE INVENTION

The present inventors have discovered a new class of chiral bidentate ligands of the formula (I) shown below capable of performing the asymmetric hydrogenation of substrates such as 1 above.

The invention also provides a new process of using said bidentate ligands performing the asymmetric hydrogenation, the process comprising

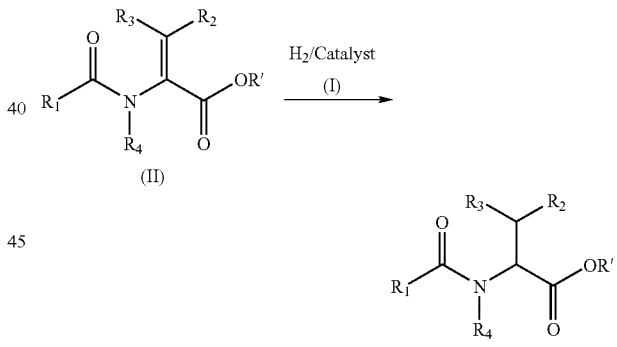

reducing a compound of the formula (II) with hydrogen in the present of a Catalyst of the formula (I);
wherein:
$R_2$ and $R_3$ are independently hydrogen, C1-5 alkyl or C2-5 alkylene, C4-6 cycloalkyl or benzyl wherein each optionally substituted by one or more $R_c$, wherein one of $R_2$ and $R_3$ can be hydrogen;
$R_c$ is C1-4 alkyl, C5-6 cycloalkyl, phenyl;
$R_1$ is alkyl, alkoxy, alkoxyalkyl, amino, alkylamino, dialkylamino, phenyl, benzyl, naphthyl, arylsulfonylC1-5alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

$R_4$ is hydrogen or C1-3 alkyl;
R' is C1-12 alkyl, benzyl, or naphthylmethyl

In a preferred embodiment:

$R_2$ and $R_3$ are independently C1-5 alkyl or C2-5 alkylene, C4-6 cycloalkyl wherein each optionally substituted by one or more $R_c$, wherein one of $R_2$ and $R_3$ can be hydrogen;

$R_c$ is C1-4 alkyl;

$R_4$ is hydrogen;

R' is methyl;

$R_1$ is morpholinyl.

Suprisingly, it was found that this can be achieved by varying three ligand design features: 1) the phosphine substituents 2) the imidazoline carbon substituents and 3) the nitrogen substituent. These ligands are of the general type shown in (2) below.

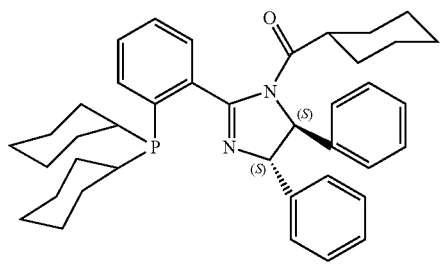

(2)

We have found that the most useful members of this ligand class contain 1) two alkyl groups on phosphorus 2) a diaryl or dicycloalkyl group on the imidazoline carbons, 3) a cyclic acyl substituent on nitrogen. The use of these ligands with a transition metal such as rhodium, iridium, or ruthenium leads to a useful chiral catalyst for asymmetric hydrogenation of C=C (alkene) bonds. It is expected that ligands of this class will also prove useful for the asymmetric hydrogenation of other unsaturated species, such as C=N (imine) and C=O (ketone) bonds.

Here, and throughout this application unless otherwise specified, the term "alkyl" refers to a saturated aliphatic radical containing from one to ten carbon atoms. "Alkyl" refers to both branched and unbranched alkyl groups. Preferred alkyl groups are straight chain alkyl groups containing from one to eight carbon atoms and branched alkyl groups containing from three to eight carbon atoms. More preferred alkyl groups are straight chain alkyl groups containing from one to six carbon atoms and branched alkyl groups containing from three to six carbon atoms. "Alkyl", as used herein, includes unsubstituted alkyl radicals, those radicals that are partially or fully halogenated and those radicals substituted with one to four, preferably one or two, substituents selected from halo, amino, cyano, nitro, methoxy, ethoxy, hydroxy, keto, carboalkoxy, or amido.

The term "cycloalkyl" refers to the cyclic analog of an alkyl group, as defined above. The cycloalkyl group can be saturated or unsaturated but not aromatic. Preferred cycloalkyl groups are saturated cycloalkyl groups containing from three to eight carbon atoms, and more preferably three to six carbon atoms. "Alkyl" and "cycloalkyl", as used herein, include unsubstituted alkyl and cycloalkyl radicals, those radicals that are partially or fully halogenated and those radicals substituted with one to four, preferably one or two, substituents selected from alkyl, halo, amino, cyano, nitro, methoxy, ethoxy, hydroxy, keto, carboalkoxy, or amido. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom.

"Aryl" refers to phenyl and naphthyl.

"Cycloacyl" as used herein shall be understood to mean the following substituent: —C(O)-cycloalkyl wherein the carbonyl group is attached to the appropriate moiety.

The term "halo" or "halogen" refers to a halogen selected from fluoro, chloro, bromo, or iodo.

The term "heteroaryl" is an aromatic monocyclic or polycyclic heteroatom containing ring. Examples of heteroaryl include but are not limited to 2-pyridyl, 3-pyridyl, 4-pyridyl, 2-furyl, 3-furyl, 2-benzofuryl, 3-benzofuryl, 2-thiophenyl, 3-thiophenyl, 2-benzothiophenyl, 3-benzothiophenyl, 2-pyrrolyl, 3-pyrrolyl, 2-indolyl, 3-indolyl, benzimidazolyl, imidazolyl, quinolinyl, isoquinolinyl, oxazolyl, benzoxazolyl, thiazolyl, and pyrimidinolyl.

The term "heteroaroyl" is an aromatic monocyclic or polycyclic heteroatom containing ring attached via a carbonyl group. Examples of heteroaroyl include but are not limited to 2-furoyl, 3-furoyl, 2-pyridoyl, 3-pyridoyl, 4-pyridoyl, 2-benzofuranoyl, 3-benzofuranoyl, 2-thiophenoyl, 3-thiophenoyl, 2-benzothiophenoyl, 3-benzothiophenoyl, 2-pyrroyl, 3-pyrroyl, 2-indoloyl, 3-indoloyl, benzimidazoyl, imidazoyl, quinolinoyl, isoquinolinoyl, oxazoyl, benzoxazoyl, thiazoyl, and pyrimidoyl.

The new chiral bidentate ligands according to the present invention is represented by Formula (I) below:

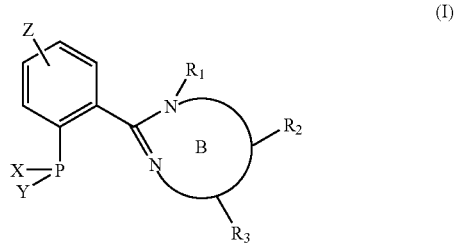

(I)

wherein:

Z is independently chosen from hydrogen, aryl (pendant (for example creating a biphenyl core) or fused (for example creating a naphthyl core)), halogen, alkyl, haloalkyl, alkoxy, cyano, nitro, amino, alkylamino, dialkylamino, —$CO_2H$, —CO($C_{1-6}$ alkoxy), —CO($C_{1-6}$alkyl), —NH-COH, —NHCO($C_{1-6}$alkyl), NHSO$_2$(alkyl), —NHSO$_2$(aryl), hydroxy, sulfonoxyalkyl, sulfonoxyaryl and alkoxyalkyl; In addition, the core ring containing the Z substituent may be one of the well-established "aryl surrogates" such as a metallocene ring, for example a ferrocene ring;

X and Y are independently chosen from alkyl and cycloalkyl wherein one of X and Y is an alkyl group, wherein if X and Y are different, the ligands will possess a stereocenter on the phosphorus atom, and this may be of the (R) or (S) absolute configuration, or a mixture of stereoisomers; wherein said X and Y may be linear or branched, and may be unsubstituted, symmetrically substituted with alkyl, aryl, or alkoxy groups, and may contain additional carbon stereocenters, or unsymmetrically substituted with alkyl, aryl, or alkoxy groups, and may contain additional carbon stereocenters; X and Y may form a fused ring system containing the phosphorus atom, such as a phosphirane, phosphetane, phospholane, or phosphinane, or a polycyclic system such as an adamantane, bicyclononane, or the like, and each ring may be unsubstituted, symmetrically substituted, or unsymmetrically substituted in all cases with alkyl, aryl, or alkoxy groups, and may contain additional carbon stereocenters; optionally each X and Y alkyl may be unsaturated and each cycloalkyl may be unsaturated but not aromatic;

R1 is chosen from hydrogen, alkyl, branched alkyl, cycloalkyl, aryl chosen from phenyl and naphthyl, heteroaryl, $C_{2-8}$ acyl, cycloacyl, aroyl chosen from the group benzoyl and naphthoyl, heteroaroyl and $SO_2R4$ where R4 is chosen from alkyl, aryl and heteroaryl, each of the above mentioned R1 is optionally substituted with one or more alkyl, halogen, haloalkyl, alkoxy, acyl, phenoxy, cyano, nitro, hydroxy, amino, alkylamino, dialkylamino, carboalkoxy, amido, or sulfoxy group;

R2 and R3 can be the same or different and can be chosen from hydrogen, aryl, heteroaryl, alkyl, branched alkyl, cycloalkyl, benzyl, substituted benzyl, each of the above mentioned R2 and R3 are independently optionally substituted with one or more alkyl, halogen, haloalkyl, alkoxy, acyl, phenoxy, cyano, nitro, hydroxy, amino, alkylamino, dialkylamino, carboalkoxy, amido, or sulfoxy group, or R2 and R3 together may form a fused carbocyclic ring;

The amidine portion must be constrained to form a ring (ring B), and said ring must be either 5- 6- or 7-membered; preferred B may be an imidazoline, tetrahydropyrimidine, or benzodiazepine ring;

wherein at least one, or both, of R2 and R3 must be attached to a chiral carbon, of either (R) or (S) absolute configuration, wherein this ring may contain another type of chiral element such as an axis or plane as well.

In another embodiment of the invention there is provided a compound of the formula (I) as provided immediately above and wherein Z is independently chosen from hydrogen, phenyl, naphthyl, halogen, C1-4 alkyl, halo C1-4 alkyl, C1-4 alkoxy, amino, C1-4 alkylamino, di-C1-4 alkylamino, —CO($C_{1-6}$ alkoxy), —CO($C_{1-6}$alkyl), —NHCOH, —NHCO($C_{1-6}$ alkyl), $NHSO_2$(C1-4 alkyl), —$NHSO_2$(phenyl), sulfonoxy C1-4 alkyl, sulfonoxyphenyl and C1-4 alkoxy C1-4 alkyl;

X and Y are independently chosen from C1-6 alkyl and C3-8cycloalkyl wherein one of X and Y is an C1-8 alkyl group, wherein if X and Y are different, the ligands will possess a stereocenter on the phosphorus atom, and this may be of the (R) or (S) absolute configuration, or a mixture of stereoisomers; wherein said X and Y may be linear, or branched, and may be unsubstituted, symmetrically substituted, or unsymmetrically substituted with alkyl or alkoxy groups, and may contain additional carbon stereocenters; X and Y may form a fused ring system containing the phosphorus atom, such as a phosphirane, phosphetane, phospholane, or phosphinane ring, each rings may be unsubstituted, symmetrically substituted, or unsymmetrically substituted with alkyl or alkoxy groups, and may contain additional carbon stereocenters; optionally each X and Y alkyl may be unsaturated and each cycloalkyl may be unsaturated but not aromatic;

R1 is chosen from hydrogen, C1-4 alkyl, branched C1-4 alkyl, C5-7 cycloalkyl, phenyl, naphthyl, heteroaryl chosen from 2-pyridyl, 3-pyridyl, 4-pyridyl, 2-furyl, 3-furyl, 2-benzofuryl, 3-benzofuryl, 2-thiophenyl, 3-thiophenyl, 2-benzothiophenyl, 3-benzothiophenyl, 2-pyrrolyl, 3-pyrrolyl, 2-indolyl, 3-indolyl, benzimidazolyl, imidazolyl, quinolinyl, isoquinolinyl, oxazolyl, benzoxazolyl, thiazolyl, and pyrimidinolyl, $C_{2-8}$ acyl, cycloacyl, aroyl chosen from the group benzoyl and napthoyl, heteroaroyl chosen from 2-furoyl, 3-furoyl, 2-pyridoyl, 3-pyridoyl, 4-pyridoyl, 2-benzofuranoyl, 3-benzofuranoyl, 2-thiophenoyl, 3-thiophenoyl, 2-benzothiophenoyl, 3-benzothiophenoyl, 2-pyrroyl, 3-pyrroyl, 2-indoloyl, 3-indoloyl, benzimidazoyl, imidazoyl, quinolinoyl, isoquinolinoyl, oxazoyl, benzoxazoyl, thiazoyl, and pyrimidoyl and $SO_2R4$ where R4 is chosen from alkyl, aryl and heteroaryl, each of the above mentioned R1 is optionally substituted with one or more alkyl, halogen, alkoxy, acyl, phenoxy, cyano, nitro, hydroxy, amino, alkylamino, dialkylamino, carboalkoxy, amido, or sulfoxy group;

R2 and R3 can be the same or different and can be chosen from hydrogen, phenyl, naphthyl, heteroaryl chosen from 2-pyridyl, 3-pyridyl, 4-pyridyl, 2-furyl, 3-furyl, 2-benzofuryl, 3-benzofuryl, 2-thiophenyl, 3-thiophenyl, 2-benzothiophenyl, 3-benzothiophenyl, 2-pyrrolyl, 3-pyrrolyl, 2-indolyl, 3-indolyl, benzimidazolyl, imidazolyl, quinolinyl, isoquinolinyl, oxazolyl, benzoxazolyl, thiazolyl, and pyrimidinolyl, C1-4 alkyl, branched C1-4 alkyl, C5-7 cycloalkyl, benzyl, substituted benzyl, each of the above mentioned R2 and R3 are independently optionally substituted with one or more alkyl, halogen, alkoxy, acyl, phenoxy, cyano, nitro, hydroxy, amino, alkylamino, dialkylamino, carboalkoxy, amido, or sulfoxy group, or R2 and R3 together may form a fused carbocyclic ring;

the amidine portion must be constrained to form a ring (ring B), and said ring must be either 5- 6- or 7-membered; preferred B may be an imidazoline, tetrahydropyrimidine, or benzodiazepine ring;

wherein at least one, or both, of R2 and R3 must be attached to a chiral carbon, of either (R) or (S) absolute configuration, wherein this ring may contain another type of chiral element such as an axis or plane as well.

The compounds of the present invention are particularly useful in asymmetric hydrogenation reactions. In such instances, preferred X,Y, would be alkyl or cycloalkyl, as described above, with C6 cycloalkyl being most preferred. Preferred Z would be hydrogen, halogen, alkyl, aryl (pendant or fused), alkoxy, haloalkyl, cyano, nitro, amino, alkylamino, and dialkylamino. Preferred R1 would be H, alkyl, benzyl, aryl, substituted aryl as described above, heteroaryl and substituted heteroaryl as described above, $C_{2-8}$ acyl, cycloacyl (optionally substituted with alkyl or alkoxy groups) and aroyl selected from the group of benzoyl, napthoyl, and pyridoyl, optionally substituted with one or more groups as described above for aryl. Preferred R2, R3 would be H, alkyl, cycloalkyl, branched alkyl, aryl and substituted aryl as described above, and heteroaryl and substituted heteroaryl as described above. Preferred B ring size might be five membered, that is, an imidazoline ring.

The phosphinoamidines of Formula (I) are electronically tunable. By varying the R1 substituent from electron withdrawing groups (e.g., acyl, benzoyl) to electron donating groups (e.g., alkyl, phenyl, benzyl), the basicity and donicity of the ligand can be easily modified and altered to suit the requirements of any given asymmetric synthesis.

In another embodiment of the invention, there is provided specific embodiments of formula (I) as follows:
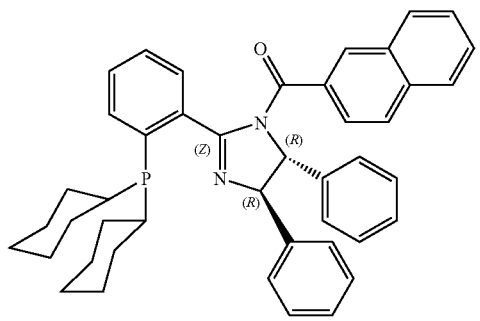
MF: C$_{44}$H$_{45}$N$_2$OP; MW: 648.81.
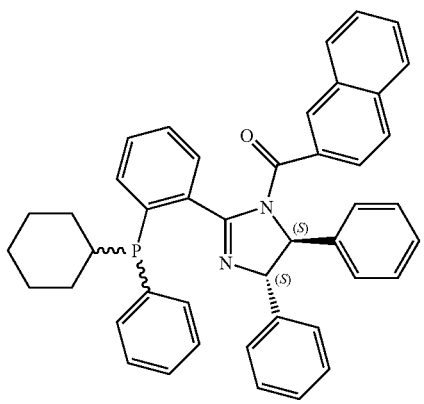
MF: C$_{44}$H$_{39}$N$_2$OP; MW: 642.77
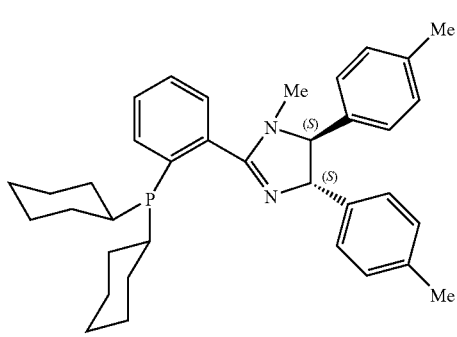
MF: C$_{36}$H$_{45}$N$_2$P; MW: 676.74.
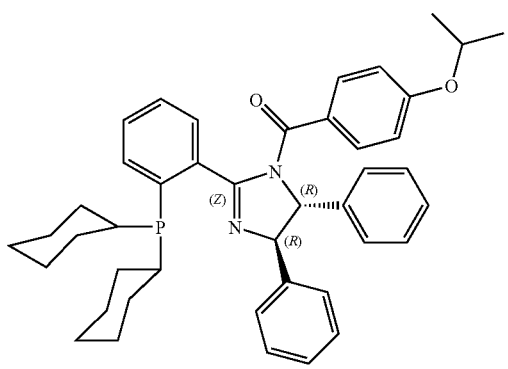
MF: C$_{43}$H$_{49}$N$_2$O$_2$P; MW: 656.84
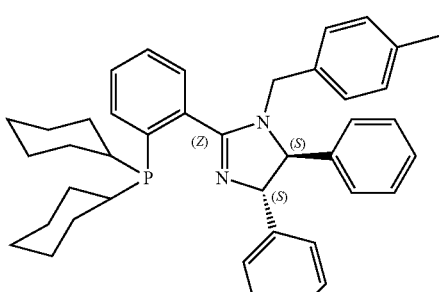
MF: C$_{41}$H$_{47}$N$_2$P; MW: 598.8.
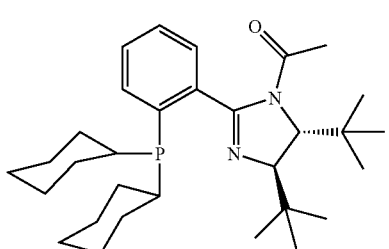
MF: C$_{31}$H$_{49}$N$_2$OP; MW: 496.71
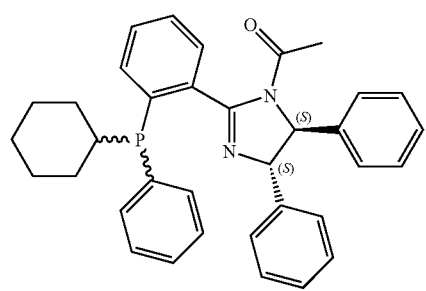
MF: C$_{35}$H$_{35}$N$_2$OP; MW: 530.64
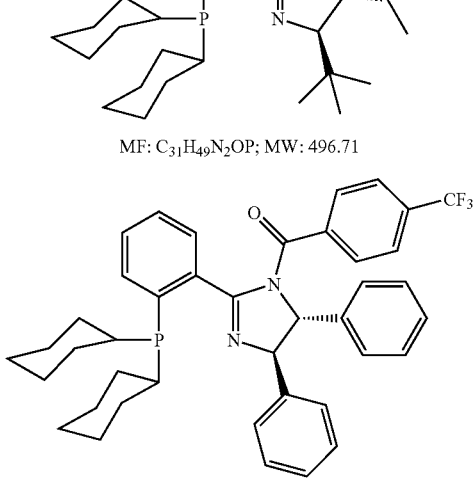
MF: C$_{41}$H$_{41}$F$_3$N$_2$OP; MW: 496.71

-continued
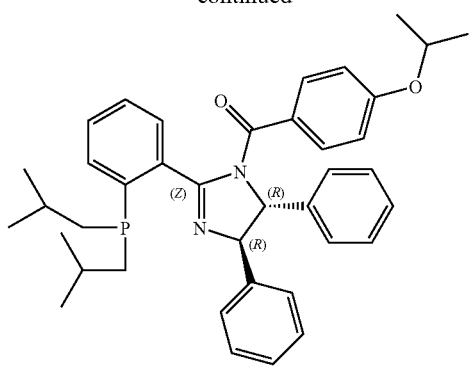
MF: C$_{39}$H$_{45}$N$_2$O$_2$P; MW: 604.76
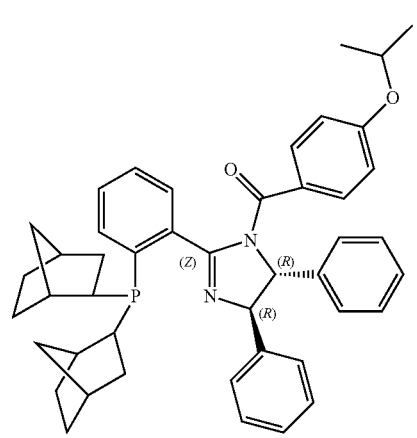
MF: C$_{45}$H$_{49}$N$_2$O$_2$P; MW: 680.86
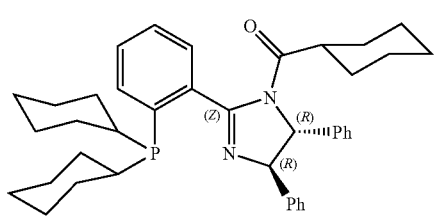
MF: C$_{40}$H$_{49}$N$_2$OP; MW: 604.80
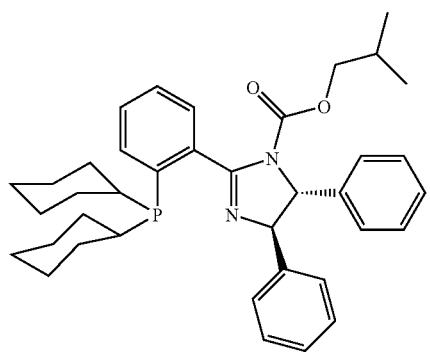
MF: C$_{38}$H$_{47}$N$_2$O$_2$P; MW: 594.77
-continued
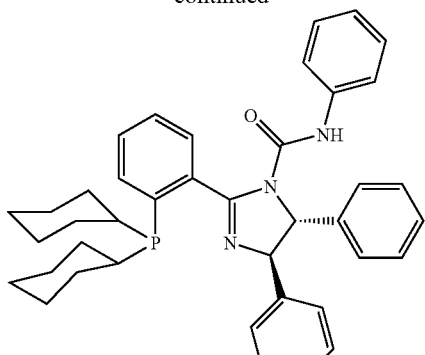
MF: C$_{40}$H$_{44}$N$_2$OP; MW: 613.77
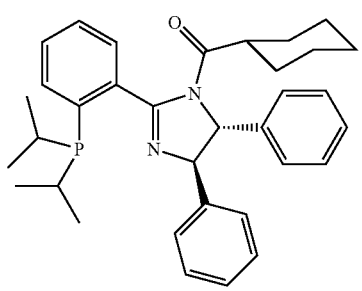
MF: C$_{34}$H$_{41}$N$_2$OP; MW: 524.68
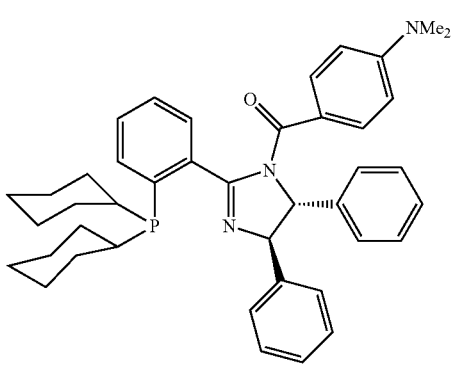
MF: C$_{42}$H$_{48}$N$_3$OP; MW: 641.82
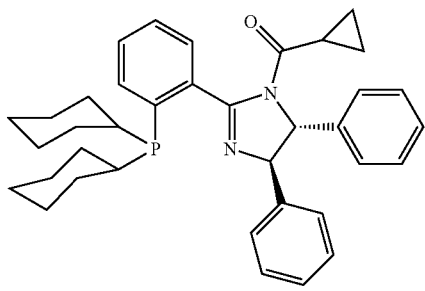
MF: C$_{37}$H$_{43}$N$_2$OP; MW: 562.72

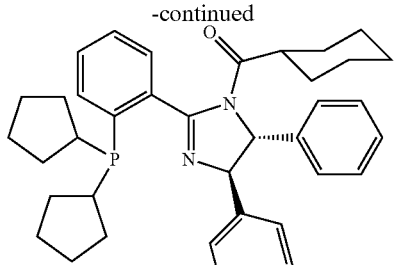
MF: C$_{38}$H$_{45}$N$_2$OP; MW: 576.75
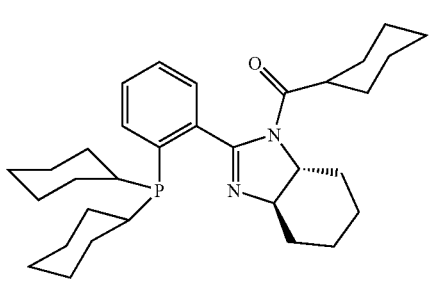
MF: C$_{32}$H$_{47}$N$_2$OP; MW: 506.7
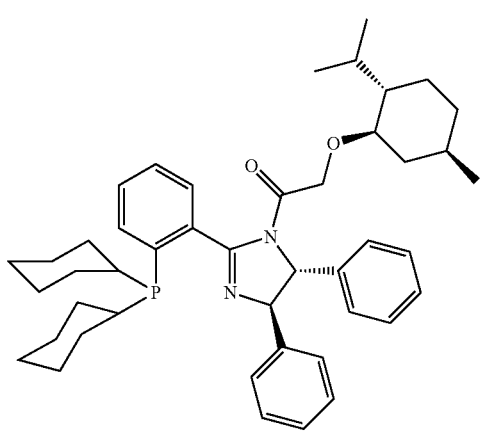
MF: C$_{45}$H$_{59}$N$_2$O$_2$P; MW: 690.94
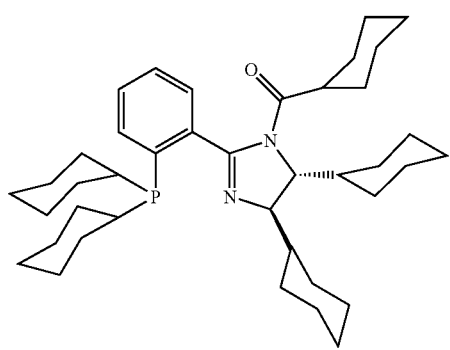
MF: C$_{40}$H$_{61}$N$_2$OP; MW: 616.90
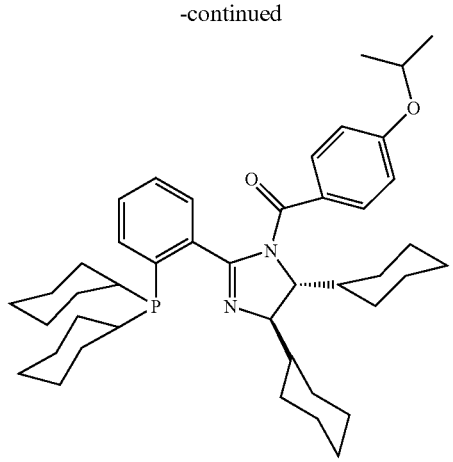
MF: C$_{43}$H$_{61}$N$_2$O$_2$P; MW: 668.93
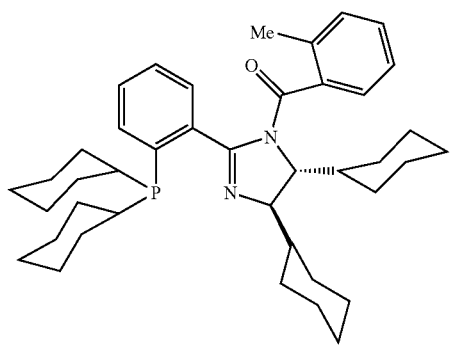
MF: C$_{41}$H$_{45}$N$_2$OP; MW: 612.78
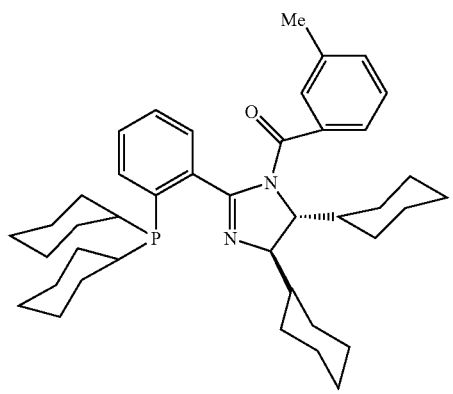
MF: C$_{41}$H$_{45}$N$_2$OP; MW: 612.78
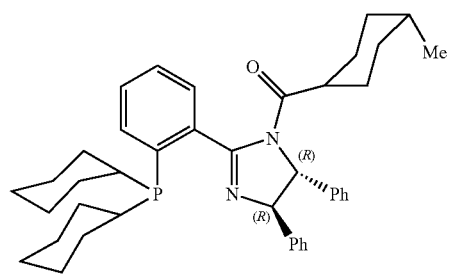
MF: C$_{41}$H$_{51}$N$_2$OP; MW: 618.83

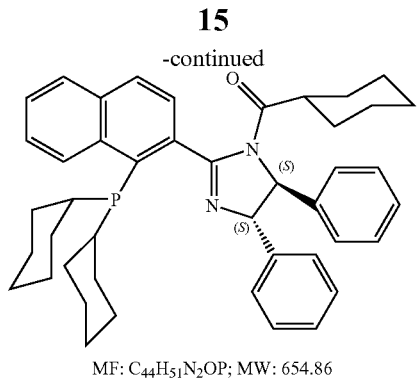

MF: C₄₄H₅₁N₂OP; MW: 654.86

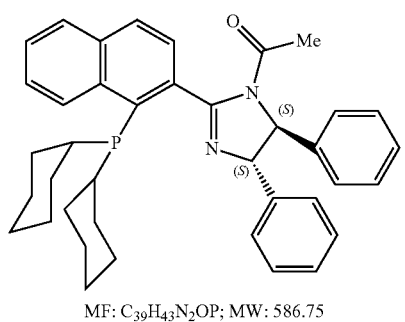

MF: C₃₉H₄₃N₂OP; MW: 586.75

To practice the instant invention, a complex is prepared between a ligand of Formula (I) and a transition metal, such as rhodium. Other transition metals such as ruthenium, iridium, nickel, palladium or platinum can be employed for catalyzed asymmetric hydrogenations. Asymmetric transformations other than hydrogenation may also be performed. For asymmetric transfer hydrogenation, rhodium, iridium, ruthenium, or lanthanides may be employed. For catalyzed, enantioselective isomerization of allyl species, rhodium or cobalt would be employed. For catalyzed asymmetric cyclopropanations, rhodium, palladium or copper would be used. For catalyzed asymmetric hydroformylations of olefins, cobalt, rhodium, platinum or palladium would be used. Rhodium would also be used for catalyzed, asymmetric hydrosilylations of ketones. Rhodium or palladium would be used in catalyzed asymmetric hydrosilylation of olefins. However, this provides only a brief list of catalyzed, asymmetric reactions where the ligands of the instant invention could be successfully used.

The complex formed using the ligands of the present invention could be isolated or could be allowed to form in situ prior to addition of the substrate molecule. In general, the reaction would be allowed to proceed under the influence of the catalyst produced by the novel ligand until completion, the product then being isolated and optical purity measured.

The phosphinoamidines of Formula (I) can be readily prepared from commercially available chiral amines or chiral amines which are themselves independently synthesized by methods known to those skilled in the art. Examples of such amines are the following:

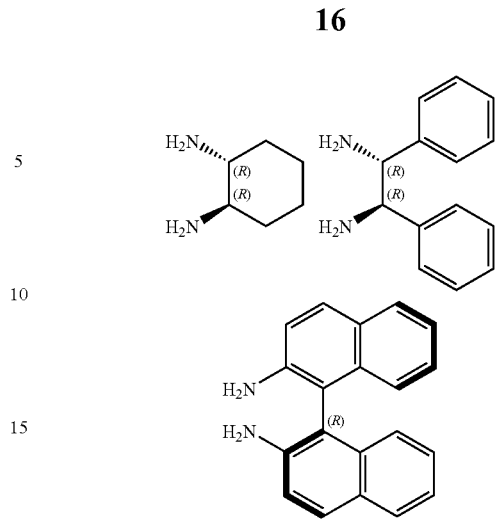

The new ligands are readily prepared, as shown in Scheme 2. Reaction of amide 4 with Meerwein's reagent furnished imidate 5 as a crystalline salt. Cyclocondensation with (R,R)-1,2-diphenylethylenediamine then yielded fluoroimidazoline 6 in good yield. Fluoride displacement with the anion of a phosphine borane provided the phosphinoimidazoline 7, and borane deprotection with DABCO gave phosphinoimidazoline 8. Ligand synthesis was completed by acylation with cyclohexanecarbonyl chloride to give phosphinoimidazoline 9, a chiral ligand of Formula (1), where X and Y are both cyclohexyl, Z is H, R1 is cyclohexylacyl, and R2 and R3 are phenyl with the (R)-stereochemistry. Reaction of this ligand with a soluble cationic rhodium complex, Rh(NBD)₂BF₄, followed by trituration with MTBE and filtration, gave chiral catalyst Rh-9 as an orange solid.

Scheme 2

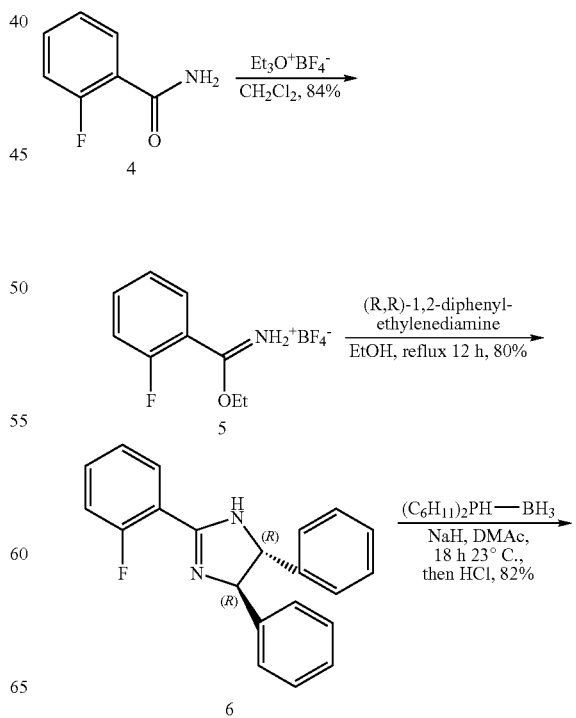

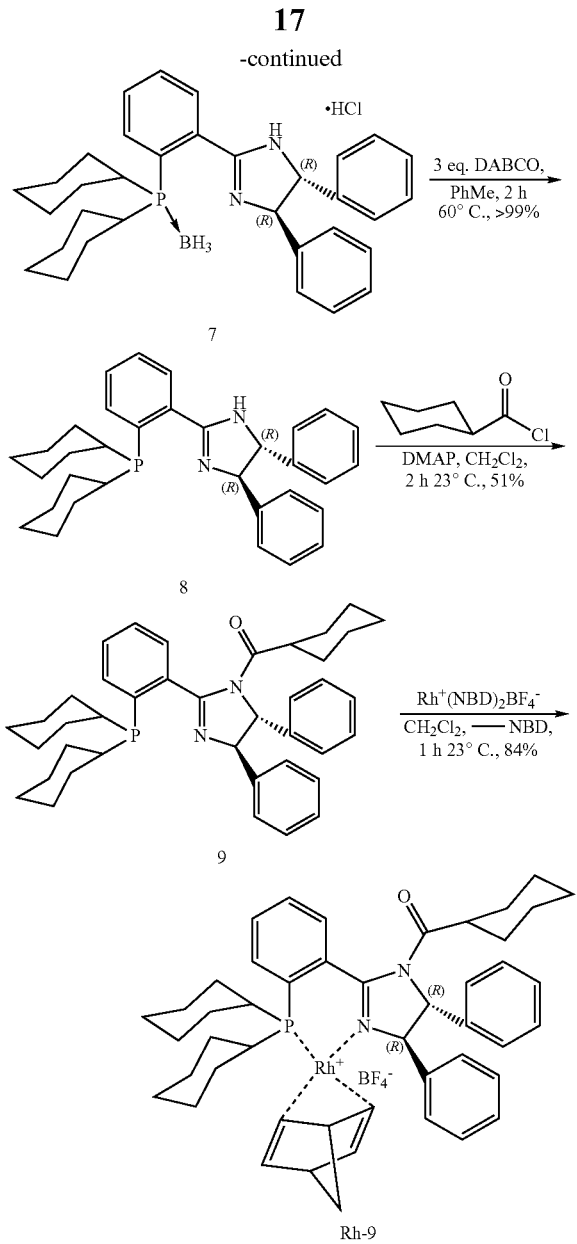

Other ligands of Formula (I) can be prepared by methods analogous to those described above.

EXPERIMENTAL SECTION

2-Fluoro-ethylbenzimidate tetrafluoroborate (5)

A 2 liter 3-neck round bottom flask was charged with 100 g 2-fluorobenzamide (0.719 mol, 1 eq.). An inert atmosphere was introduced by two vacuum/argon cycles. 863 mL 1 M Meerwein's/CH$_2$Cl$_2$ solution (0.863 mol, 1.2 eq.) was then added to the flask via canula under N$_2$ pressure, giving initially a slurry which became a clear solution after ~30 minutes. After ~4 hours stirring at 23° C. under argon, a slurry was again present. The mixture was stirred for a total of 16 hours at 23° C. under argon, then it was poured quickly into a large flask and the CH$_2$Cl$_2$ removed at the rotovap, giving an off-white solid. This solid was then suspended in 250 mL EtOAc, heated briefly at reflux (~30 seconds), then the resultant slurry was filtered while still warm under N$_2$ on a corase-fritted funnel. After drying on the frit under a vigorous flow of N$_2$ for one hour, 155 g 2-fluorobenzimidate 5 (84%) was obtained as a colorless solid. It was immediately bottled and placed in a desiccator. M.p. 128-131° C.; $^{19}$F NMR (DMSO) δ: −113.8, −154.2 ppm.

Fluoroimidazoline (6):

A 2 liter 3-neck round bottom flask was charged with 50.0 g (R,R)-1,2-diphenylethylendiamine (0.236 mol, 1 eq.), 60.0 g imidate 5 (0.236 mol, 1 eq.), and 700 mL absolute EtOH. The resulting mixture was then stirred one hour at 23° C. under Ar, then heated to reflux and maintained at that temperature for 16 hours. The mixture was then cooled to 23° C., and the EtOH was removed in vacuo. The residue was then partitioned between 500 mL 1 N NaOH and 500 mL EtOAc. The phases were separated and the aqueous phase re-extracted with 300 mL EtOAc. The combined organic phases were dried (MgSO$_4$), and the solvents removed in vacuo to give a yellow solid. This solid was suspended in 500 mL boiling hexane, and EtOAc (100 mL) was added until a clear solution was obtained. The supernatant solution was decanted from a small amount of insoluble material and allowed to cool to 23° C., causing a thick slurry to form. This slurry was cooled to 0° C. and filtered, and the solid was dried 30 minutes at 50° C./1 mm to give 46 g fluoroimidazoline 6 as a colorless solid. The mother liquors were concentrated to give a solid which was recrystallized from EtOAc to give a further 14 g of 6. Overall yield 60 g, 80%, as white crystals. Mp 119° C.; $^1$H NMR (400 MHz, CDCl$_3$) δ: 8.31 (td, J=7.7, 1.7 Hz, 1H), 7.48 (m, 1H), 7.32 (m, 11H), 7.17 (ddd, J=12.0, 8.3, 0.9 Hz, 1H), 6.04 (broad s, 1H), 4.92 (s, 2H). $^{13}$C NMR (100 MHz, CDCl$_3$) δ: 160.9 (s, $^1J_{CF}$=250 Hz), 159.3 (d, $J_{CF}$=2 Hz), 143.3 (s), 132.6 (d, $J_{CF}$=9 Hz), 131.4 (d), 128.7 (d), 127.5 (d), 126.6 (d), 124.6 (d, $J_{CF}$=3 Hz), 117.6 (d, $J_{CF}$=10 Hz), 116.1 (d, $J_{CF}$=23 Hz), 74.6 (d). $^{19}$F NMR (376 MHz, CDCl$_3$) δ: −113.40. MS (M+H)$^+$ 317.5. Anal. Calcd for C$_{21}$H$_{17}$FN$_2$: C, 79.72; H, 5.42; F, 6.01; N, 8.85. Found C, 79.56; H, 5.38; N, 8.73.

Phosphinoborane (7):

A 4-neck 3 L round bottom flask with mechanical stirrer, thermocouple, and 500 mL addition funnel was charged with 148 g dicyclohexylphosphine borane (0.70 mol, 2.22 eq.), then evacuated/Ar filled (2×). 400 mL DMAc was then charged to the addition funnel via canula under N$_2$ pressure, then added at once to the batch. The internal temperature fell to a minimum of 18.6° C., and after stirring 10 minutes, the internal temperature of the thin slurry was 20.0° C. The flask was then cooled with a cool H$_2$O bath. 27.8 g 60% NaH in oil (0.70 mol, 2.22 eq.) was then added in five portions about five minutes apart, causing immediate gas evolution and an exotherm to a maximum of 37° C. 10 minutes after completion of the addition. After stirring for 45 minutes after completion of the NaH addition, the reactor was cooled in an ice bath. A solution of 100 g fluoroimidazoline 4 (0.316 mol, 1 eq.) in 190 mL DMAc was then charged to the addition funnel. The batch temperature was 2.8° C. The fluoride solution was then added dropwise over ~20 minutes, causing some additional gas evolution, and forming an orange reaction mixture. The maximum batch temperature reached during the addition was 5.0° C. The ice bath was then removed and the reaction mixture allowed to warm. The batch reached a maximum temperature of 29.9° C. two hours after completion of the fluoride solution addition. 20 mL additional DMAc was used to wash the walls of the addition funnel into the flask. The resulting orange mixture, nearly a clear solution, was then stirred at ~23° C. under Ar for 14 hours. 400 mL MTBE was then added, and the mixture cooled in an ice bath. A solution of 400 mL 5M NH$_4$Cl was then added charged to the addition funnel. At an internal batch temperature of 4.5° C., the NH$_4$Cl solution was added dropwise over ~20 minutes, causing an exotherm to 18° C. The pH was observed to be 8.5. The addition funnel was then charged with 400 mL 4N HCl, and a pH probe was inserted in one of the necks. Dropwise addition of the 4N HCl solution was then started (initial batch temperature 11° C.) while closely monitoring the pH. When pH 4.5 was reached, a significant slurry began to develop, and the rate of addition of 4 N HCl was slowed. When the batch pH reached 4.0, acid addition was stopped: 250 mL 4 N HCl had been added, and a thick slurry was present. The slurry was agitated vigorously for 20 minutes, then filtered through a coarse-fritted funnel, using 400 mL 0.4N HCl to transfer the slurry. The voluminous filter cake was then washed with $H_2O$ (1×1 L), allowing the $H_2O$ to stand on the cake for ~5 minutes before sucking it through the cake. When the liquors had largely stopped flowing through the cake, IL MTBE was added, allowed to stand, and then sucked through the cake as before. After ~30 minutes on the frit, the filter cake was transferred back to the reactor and 1.5 L MTBE was added. The resultant slurry was agitated vigorously for 30 minutes, then filtered under $N_2$, giving a filter cake with a much smaller volume than the original filter cake. After drying under $N_2$ on the frit for one hour, the solid was transferred to a vacuum oven and dried at 70° C./1 mm for three hours, giving 160 g of a white solid with KF=0.3% $H_2O$. A final purification with THF was then carried out: The solid was suspended in 250 mL THF and agitated vigorously for 30 minutes. The slurry was then filtered under $N_2$, and dried on the frit under $N_2$ for one hour to give 142 g phosphine borane 5 as its HCl salt (82%) as a colorless powder. HPLC purity (C18) >99%. Chiral HPLC: Chiralpak IA, 4.6×250 mm, 25° C., 96:4 Heptane:i-PrOH, 2.0 mL/min., 5 μL injection, 254 nm) showed >99.5% ee: Retention time 6.45 minutes. This material was used without further purification. An analytical sample was prepared by recrystallized from boiling 1:1 $MeCN:H_2O$, giving the crystalline MeCN solvate. M.p. 177-180° C.; $[\alpha]^{20}_D=-82$ (c 0.55, MeOH). $^1H$ NMR (500 MHz, acetone d6) δ: 8.17 (dd, J=7.8, 13.1 Hz, 1H), 7.88 (d, J=7.7 Hz, 1H), 7.64 (t, J=7.5 Hz, 1H), 7.59-7.54 (m, 3H), 7.49 (d, J=7.6 Hz, 2H), 7.45-7.40 (m, 4H), 7.35 (m, 2H), 7.12 (br s, 1H), 5.19 (d, J=10.7 Hz, 1H), 5.13 (dd, J=1.9, 10.7 Hz, 1H), 3.06 (m, 1H), 2.95 (m, 1H), 1.83 (m, 2H), 1.72 (br s, 2H), 1.60 (m, 6H), 1.35-1.16 (m, 10H), 0.70 (m, 3H). $^{31}P$ NMR (202 MHz, MeOH d4) δ: 31.00 (HCl salt). HRMS $(M+H)^+$ $C_{33}H_{43}BN_2P$: calculated 509.3251, observed 509.3262, difference=2.0716 ppm.

(R,R)-Phosphinoimidazoline (8):

A 250 mL round bottom flask was charged with 5.08 g phosphinoborane 7 (10.0 mmol, 1 eq.), 3.36 g DABCO (30.0 mmol, 3 eq.), and 60 mL toluene. The resulting mixture was heated at 60° C. for two hours, then cooled to 23° C. The toluene was removed in vacuo, and the residue dissolved in 50 mL EtOAc and filtered through a short column of silica gel, eluting with a further 150 mL EtOAc. The EtOAc was then removed in vacuo and the residue dried under high vacuum to give 5.35 g phosphinoimidazoline (R,R)-8 (~100%) as a sticky oil. $^1H$ NMR (500 MHz, $CD_3OD$) δ: 7.93 (d, J=7.6 Hz, 1H), 7.86 (dd, J=7.5, 1.6 Hz, 1H), 7.77 (t, J=6.7 Hz, 1H), 7.71 (t, J=7.6 Hz, 1H), 7.62 (m, 4H), 7.59-7.48 (m, 6H), 5.39 (s, 2H), 2.19-2.11 (m, 2H), 2.06 (d, J=9.1 Hz, 2H), 1.86 (d, J=12.6 Hz, 2H), 1.77-1.66 (m, 4H), 1.61 (t, J=12.1 Hz, 2H), 1.51-1.16 (m, 10H). $^{13}C$ NMR (125 MHz, $CD_3OD$) δ: 139.79, 137.76 ($J_{CP}$=24 Hz), 135.45 ($J_{CP}$=3.1 Hz), 133.75 ($J_{CP}$=33 Hz), 133.08, 131.17, 130.68, 130.61, 129.80 ($J_{CP}$=6.9 Hz), 128.61 ($J_{CP}$=2.8 Hz), 72.46, 35.89 ($J_{CP}$=13 Hz), 35.79 ($J_{CP}$=11.9 Hz), 32.27, 32.12, 31.98, 31.10 ($J_{CP}$=8.7 Hz), 30.86 ($J_{CP}$=8.6 Hz), 28.26, 28.15, 28.13, 28.08, 28.07, 28.03, 27.59 ($J_{CP}$=6.1 Hz). $^{31}P$ NMR (202 MHz, $CD_3OD$) δ: −6.68. HRMS $(M+H)^+$ $C_{33}H_{40}N_2P$: calculated 495.2923, observed 495.2912, difference=2.3510 ppm.

(R,R)-Phosphinoimidazoline 9:

A 100 mL round bottom flask was charged with 0.77 g phosphinoimidazoline (R,R)-8 (1.56 mmol, 1 eq.), 0.38 g DMAP (3.12 mmol, 2 eq.), 20 mL $CH_2Cl_2$ and 0.209 mL cyclohexane carbonylchloride (1.56 mmol, 1 eq.) in the order given. The resulting mixture was stirred one hour at 23° C., then 20 microliters of N,N,N'-trimethylethylenediamine was added to scavenge unreacted acid chloride. After 15 minutes, $CH_2Cl_2$ was removed in vacuo, and the residue was partitioned between 25 mL EtOAc and 25 mL 0.5 N HCl. The organic phase was then washed with saturated $NaHCO_3$ (1×25 mL), dried ($MgSO_4$) and the solvents removed in vacuo to give a yellow oil. This oil was then chromatographed on silica gel eluting with 5:1 hexane:EtOAc, saving only the center fractions, to give an oil. This oil was then azeotroped with $Et_2O$ (2×15 mL), and then dried under high vacuum to give 0.48 g (R,R)-9 (51%) as a colorless foam. MS $(M+H)^+$ 605.2 (EM: 604.4); $^1H$ NMR (500 MHz, MeOH $d_4$) δ: 7.72 (m, 2H), 7.61 (m, 2H), 7.52 (m, 3H), 7.44 (m, 4H), 7.36 (m, 3H), 5.30 (s, 1H), 5.01 (d, J=6.5 Hz, 1H), 2.20-0.60 (m, 33H). $^{31}P$ NMR (202 MHz, MeOH $d_4$) δ: −7.15.

(R,R)-Rh-9: A 50 mL round bottom flask was charged with 280 mg (R,R)-9 (0.463 mmol, 1 eq.), 173 mg $Rh^+(NBD)_2$ $BF_4^-$ (0.463 mmol, 1 eq.), and 7.0 mL $CH_2Cl_2$. The resulting red solution was stirred one hour at 23° C. under Ar, then the $CH_2Cl_2$ was removed in vacuo. The residue was scraped from the walls of the flask, triturated with $Et_2O$, and filtered. The resulting solid was then pulverized under $Et_2O$ on the frit, refiltered, and air-dried 30 minutes to give 0.344 g (R,R)-Rh-9 (84%) as an orange powder. $^{31}P$ NMR (202 MHz, MeOH d4) δ: 25.32 (d, $J_{P-Rh}$=152 Hz).

Typical uses of the invention in asymmetric synthesis are shown in Schemes 3 and 4 below.

Scheme 3

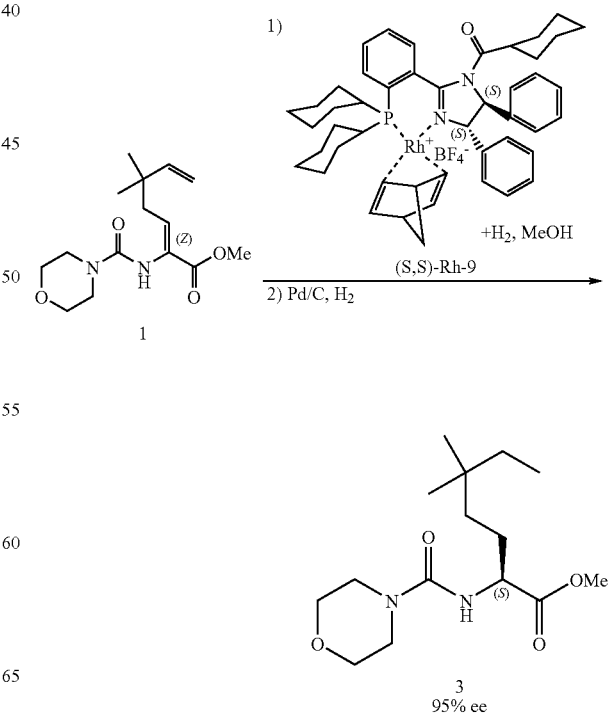

Rhodium-Catalyzed Asymmetric Hydrogenation of Olefin 1 with (S,S)-9:

MeOH was degassed by bubbling $N_2$ through it for 15 minutes, then 148 mg olefin 1 (0.50 mmol, 1 eq.) was dissolved in 2.0 mL degassed MeOH. In a separate vial, 4.6 mg (S,S)-Rh-9 (0.005 mmol, 0.01 eq.) was dissolved in 1.0 mL degassed MeOH. To this vial was added the olefin solution. The vial was then placed in a pressure vessel, pressurized to 100 psi with $H_2$, and the atmosphere exchanged for $H_2$ four times. The vessel was then again pressurized to 100 psi with $H_2$, and then stirred for 20 hours at 23° C. The vessel was opened and 5 mg 10% Pd/C was added to the vial. The vessel atmosphere was exchanged with $H_2$ as described above, then pressurized to 200 psi with $H_2$ and stirred for four hours at 23° C. The vessel was opened, and the vial contents chromatographed on silica gel eluting with $CH_2Cl_2$/MeOH in a gradient from 0% MeOH to 10% MeOH on a Combiflash automated chromatography unit to give 133 mg saturated product 3 (90%) as a colorless solid. Chiral HPLC (Chiralcel AD-H, 75:25 heptane:n-PrOH) showed 95% ee (S).

Scheme 4

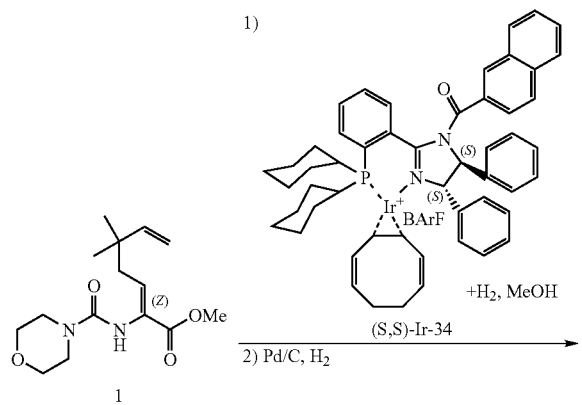

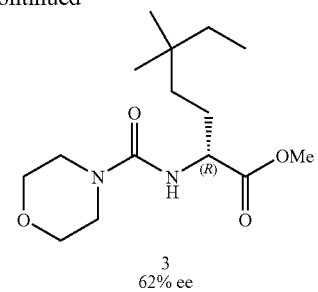

3
62% ee

Iridium-Catalyzed Asymmetric Hydrogenation of Olefin 1 with (S,S)-34:

$CH_2Cl_2$ was degassed by bubbling $N_2$ through it for 15 minutes, then 100 mg olefin 1 (0.338 mmol, 1 eq.) was dissolved in 1.0 mL degassed $CH_2Cl_2$. In a separate vial, 6.2 mg (S,S)-Ir-34 (0.0034 mmol, 0.01 eq.) was dissolved in 1.0 mL degassed $CH_2Cl_2$. To this vial was added the olefin solution. The vial was then placed in a pressure vessel, pressurized to 250 psi with $H_2$, and the atmosphere exchanged for $H_2$ four times. The vessel was then again pressurized to 250 psi with $H_2$, and then stirred for 20 hours at 23° C. The vessel was opened and 5 mg 10% Pd/C was added to the vial. The vessel atmosphere was exchanged with $H_2$ as described above, then pressurized to 200 psi with $H_2$ and stirred for four hours at 23° C. The vessel was opened, and the vial contents chromatographed on silica gel eluting with $CH_2Cl_2$/MeOH in a gradient from 0% MeOH to 10% MeOH on a Combiflash automated chromatography unit to give 90 mg saturated product 3 (90%) as a colorless solid. Chiral HPLC (Chiralcel AD-H, 75:25 heptane:n-PrOH) showed 62% ee (R).

Table 1 shows results for 22 of the new ligands when evaluated in the asymmetric hydrogenation reaction.

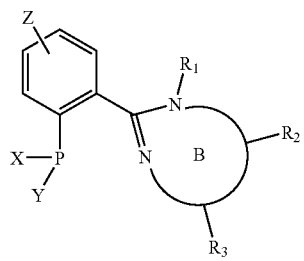

(I)

| X | Y | Z | $R_1$ | $R_2$ | $R_3$ | B* | M | % ee |
|---|---|---|---|---|---|---|---|---|
| Ph | cHex | H | 4-isopropoxy benzoyl | Ph | Ph | 5 | Rh | NR |
| cHex | cHex | H | 4-isopropoxy benzoyl | Ph | Ph | 5 | Rh | 85 |
| norbornyl | norbornyl | H | 4-isopropoxy benzoyl | Ph | Ph | 5 | Rh | 14 |
| i-Bu | i-Bu | H | 4-isopropoxy benzoyl | Ph | Ph | 5 | Rh | NR |
| i-Pr | i-Pr | H | 4-isopropoxy benzoyl | Ph | Ph | 5 | Rh | 17 |
| cPent | cPent | H | 4-isopropoxy benzoyl | Ph | Ph | 5 | Rh | 0 |
| cHex | cHex | H | 4-methylbenzyl | Ph | Ph | 5 | Rh | 10 |

-continued

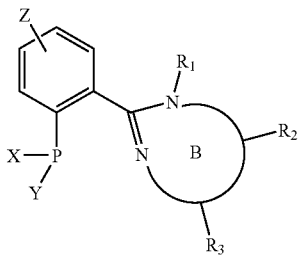

(I)

| X | Y | Z | R₁ | R₂ | R₃ | B* | M | % ee |
|---|---|---|---|---|---|---|---|---|
| cHex | cHex | H | Me | Ph | Ph | 5 | Rh | NR |
| cHex | cHex | H | Ac | Ph | Ph | 5 | Rh | 94 |
| cHex | cHex | H | 4-CF₃ benzoyl | Ph | Ph | 5 | Rh | 71 |
| cHex | cHex | H | 4-NMe₂ benzoyl | Ph | Ph | 5 | Rh | 13 |
| cHex | cHex | H | cHex carbonyl | Ph | Ph | 5 | Rh | 95 |
| cHex | cHex | C₄H₄ (naphthyl) | Ac | Ph | Ph | 5 | Rh | 98 |
| cHex | cHex | C₄H₄ (naphthyl) | cHex carbonyl | Ph | Ph | 5 | Rh | >99 |
| cHex | cHex | H | cProp carbonyl | Ph | Ph | 5 | Rh | 10 |
| cHex | cHex | H | CO₂-i-Bu | Ph | Ph | 5 | Rh | 9 |
| cHex | cHex | H | CONHPh | Ph | Ph | 5 | Rh | 8 |
| cHex | cHex | H | 2-naphthoyl | Ph | Ph | 5 | Ir | 62 |
| cHex | cHex | H | 2-Me benzoyl | Ph | Ph | 5 | Rh | 11 |
| cHex | cHex | H | 3-Me benzoyl | Ph | Ph | 5 | Rh | 14 |
| cHex | cHex | H | cHex carbonyl | —(CH₂)₄— | —(CH₂)₄— | 5 | Rh | 4 |
| cHex | cHex | H | cHex carbonyl | cHex | cHex | 5 | Rh | 73 |
| cHex | cHex | H | 4-isopropoxy benzoyl | cHex | cHex | 5 | Rh | 60 | wherein c represents "cyclo", for example cHex = cyclohexyl, "i" = iso.
*ring size While in the foregoing description the detailed embodiments of the present invention have been set forth, it will be understood by those skilled in the art that considerable variation may be made in such detail without departing from the spirit of the invention.

All literature and patent publications cited in this application are incorporated herein by reference in their entirety.

The invention claimed is:

1. A chiral bidentate ligands of the Formula (I) below:

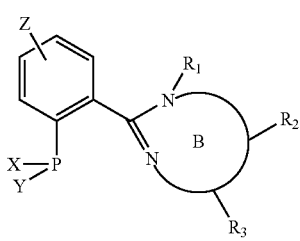

(I)

wherein:

Z is independently chosen from hydrogen, aryl ring optionally fused with the phenyl ring. heteroaryl, halogen, alkyl, haloalkyl, alkoxy, cyano, nitro, amino, alkylamino, dialkylamino, —CO₂H, —CO(C₁₋₆ alkoxy), —CO(C₁₋₆alkyl), —NHCOH, —NHCO(C₁₋₆alkyl), NHSO₂(alkyl), —NHSO₂(aryl), hydroxy, sulfonoxyalkyl, sulfonoxyaryl and alkoxyalkyl;

X and Y are independently chosen from alkyl and cycloalkyl wherein one of X and Y is an alkyl group, wherein if X and Y are different, the ligands will possess a stereocenter on the phosphorus atom, and this may be of the (R) or (S) absolute configuration, or a mixture of stereoisomers; wherein said X and Y may be a linear or branched alkyl group, which may be unsubstituted or symmetrically substituted with alkyl, aryl, or alkoxy groups, and may contain additional carbon stereocenters, or unsymmetrically substituted with alkyl, aryl, or alkoxy groups, and may contain additional carbon stereocenters; X and Y together with a phosphorus atomb may form a ring system, wherein the ring system may be unsubstituted, symmetrically substituted, or unsymmetrically substituted with alkyl, aryl, or alkoxy groups, and may contain additional carbon stereocenters; optionally each X and Y alkyl may be unsaturated and each cycloalkyl may be unsaturated but not aromatic;

R1 is chosen from hydrogen, alkyl, branched alkyl, cycloalkyl, aryl chosen from phenyl and naphthyl, heteroaryl, C₂₋₈ acyl, cycloacyl, aroyl chosen from the group benzoyl and naphthoyl, and heteroaroyl, each of the above mentioned R1 is optionally substituted with one or more alkyl, halogen, haloalkyl, alkoxy, acyl, phenoxy, cyano, nitro, hydroxy, amino, alkylamino, dialkylamino, carboalkoxy, amido or sulfoxy group;

R2 and R3 can be the same or different and can be chosen from hydrogen, aryl, heteroaryl, alkyl, branched alkyl, cycloalkyl, benzyl, substituted benzyl, each of the above mentioned R2 and R3 are independently optionally substituted with one or more alkyl, halogen, haloalkyl, alkoxy, acyl, phenoxy, cyano, nitro, hydroxy, amino, alkylamino, dialkylamino, carboalkoxy, amido, or sulfoxy group, or R2 and R3 together may form a fused carbocyclic ring;

wherein Ring B represents a 5-membered ring;

wherein at least one, or both, of R2 and R3 must be attached to a chiral carbon, of either (R) or (S) absolute configuration, wherein this ring may contain another type of chiral element.

2. The compound of according to claim 1 wherein

Z is independently chosen from hydrogen, phenyl, naphthyl, halogen, C1-4 alkyl, halo C1-4 alkyl, C1-4 alkoxy, amino, C1-4 alkylamino, di-C1-4 alkylamino, —CO($C_{1-6}$ alkoxy), —CO($C_{1-6}$alkyl), —NHCOH, —NHCO($C_{1-6}$alkyl), NHSO$_2$(C1-4 alkyl), —NHSO$_2$(phenyl), sulfonoxy C1-4 alkyl, sulfonoxyphenyl and C1-4 alkoxy C1-4 alkyl;

X and Y are independently chosen from C1-6 alkyl and C3-8 cycloalkyl wherein one of X and Y is an C1-8 alkyl group, wherein if X and Y are different, the ligands will possess a stereocenter on the phosphorus atom, and this may be of the (R) or (S) absolute configuration, or a mixture of stereoisomers; wherein said X and Y may be a linear, or branched, alkyl group, which may be unsubstituted, symmetrically substituted, or unsymmetrically substituted with alkyl or alkoxy groups, and may contain additional carbon stereocenters; X and Y together with a phosphorus atom may form a ring system wherein the ring system may be unsubstituted, symmetrically substituted, or unsymmetrically substituted with alkyl or alkoxy groups, and may contain additional carbon stereocenters; optionally each X and Y alkyl may be unsaturated and each cycloalkyl may be unsaturated but not aromatic;

R1 is chosen from hydrogen, C1-4 alkyl, branched C1-4 alkyl, C5-7 cycloalkyl, phenyl, naphthyl, heteroaryl chosen from 2-pyridyl, 3-pyridyl, 4-pyridyl, 2-furyl, 3-furyl, 2-benzofuryl, 3-benzofuryl, 2-thiophenyl, 3-thiophenyl, 2-benzothiophenyl, 3-benzothiophenyl, 2-pyrrolyl, 3-pyrrolyl, 2-indolyl, 3-indolyl, benzimidazolyl, imidazolyl, quinolinyl, isoquinolinyl, oxazolyl, benzoxazolyl, thiazolyl, and pyrimidinolyl, $C_{2-8}$ acyl, cycloacyl, aroyl chosen from the group benzoyl and napthoyl, heteroaroyl chosen from 2-furoyl, 3-furoyl, 2-pyridoyl, 3-pyridoyl, 4-pyridoyl, 2-benzofuranoyl, 3-benzofuranoyl, 2-thiophenoyl, 3-thiophenoyl, 2-benzothiophenoyl, 3-benzothiophenoyl, 2-pyrroyl, 3-pyrroyl, 2-indoloyl, 3-indoloyl, benzimidazoyl, imidazoyl, quinolinoyl, isoquinolinoyl, oxazoyl, benzoxazoyl, thiazoyl, and pyrimidoyl and SO$_2$R4 where R4 is chosen from alkyl, aryl and heteroaryl, each of the above mentioned R1 is optionally substituted with one or more alkyl, halogen, alkoxy, acyl, phenoxy, cyano, nitro, hydroxy, amino, alkylamino, dialkylamino, carboalkoxy, amido or sulfoxy group;

R2 and R3 can be the same or different and can be chosen from hydrogen, phenyl, naphthyl, heteroaryl chosen from 2-pyridyl, 3-pyridyl, 4-pyridyl, 2-furyl, 3-furyl, 2-benzofuryl, 3-benzofuryl, 2-thiophenyl, 3-thiophenyl, 2-benzothiophenyl, 3-benzothiophenyl, 2-pyrrolyl, 3-pyrrolyl, 2-indolyl, 3-indolyl, benzimidazolyl, imidazolyl, quinolinyl, isoquinolinyl, oxazolyl, benzoxazolyl, thiazolyl, and pyrimidinolyl, C1-4 alkyl, branched C1-4 alkyl, C5-7 cycloalkyl, benzyl, substituted benzyl, each of the above mentioned R2 and R3 are independently optionally substituted with one or more alkyl, halogen, alkoxy, acyl, phenoxy, cyano, nitro, hydroxy, amino, alkylamino, dialkylamino, carboalkoxy, amido, or sulfoxy group, or R2 and R3 together may form a fused carbocyclic ring;

Wherein Ring B represents a 5-membered ring, and said ring is an imidazoline, tetrahydropyrimidine or benzodiazepine ring;

wherein at least one, or both, of R2 and R3 must be attached to a chiral carbon, of either (R) or (S) absolute configuration, wherein this ring may contain another type of chiral element.

3. The compound of according to claim 2 wherein

X is phenyl, cyclohexyl, norbornyl, i-butyl, i-propyl or cyclopentyl;

Y is phenyl, cyclohexyl, norbornyl, i-butyl, i-propyl or cyclopentyl;

Z is hydrogen or fused with the phenyl ring to form naphthyl;

R1 is 4-isopropoxybenzoyl, 4-methylbenzyl, methyl, acetyl, 4-CF$_3$-benzoyl, 4-N(CH$_3$)$_2$, benzoyl, cyclohexylcarbonyl, cyclopropylcarbonyl, —CO$_2$-i-Bu, —CONH(phenyl), 2-naphthoyl, 2-methylbenzoyl or 3-methylbenzoyl;

R2 is —(CH$_2$)$_4$—, phenyl or cyclohexyl; and

R3 is —(CH$_2$)$_4$—, phenyl or cyclohexyl.

4. A compound chosen from

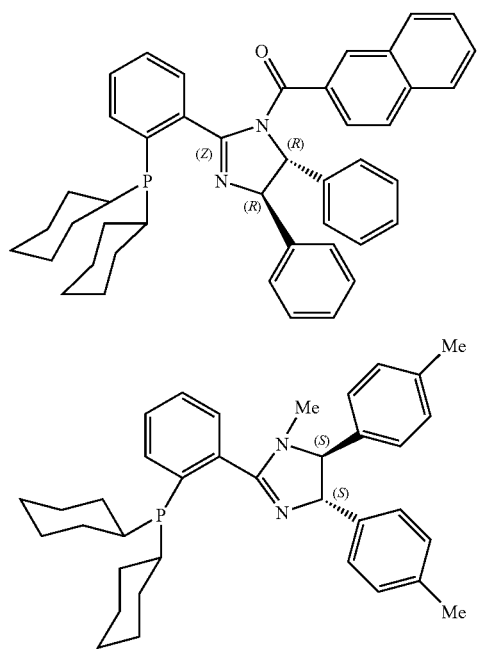

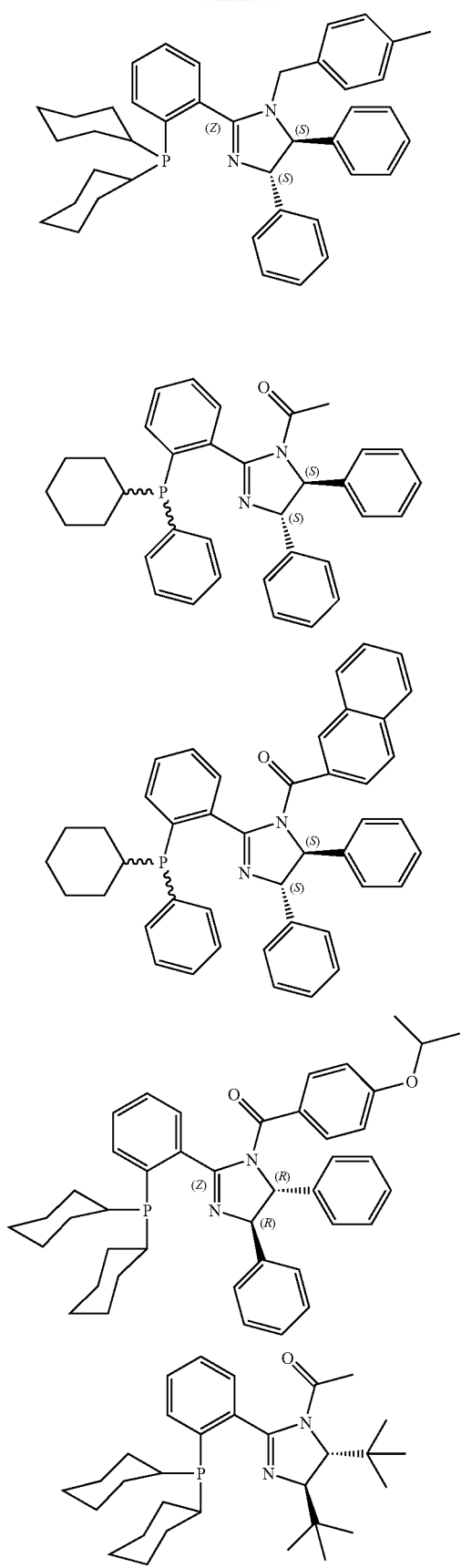
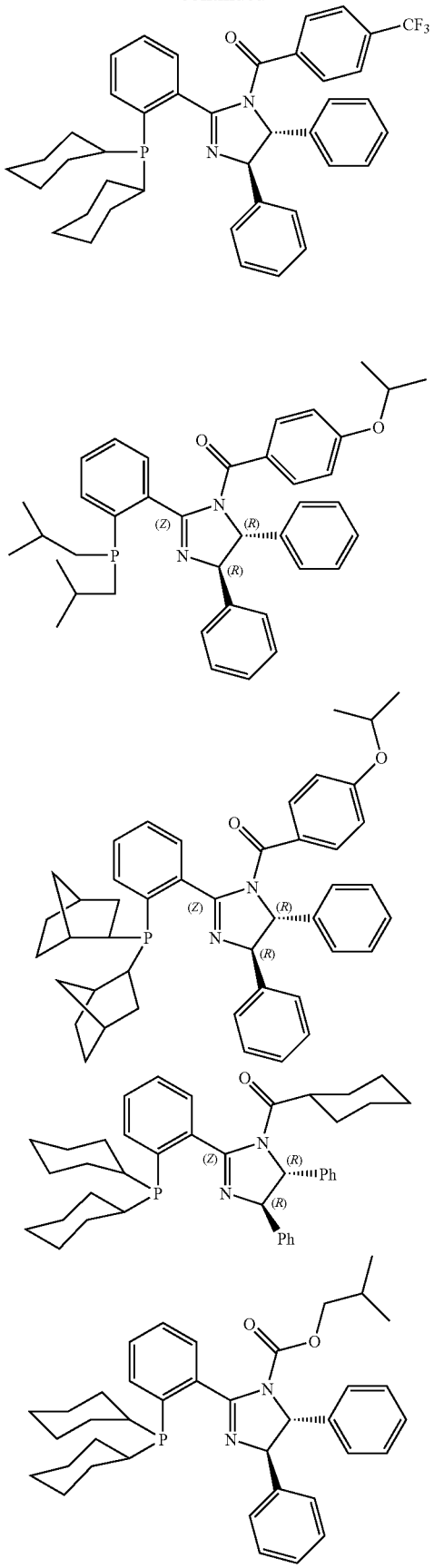

29
-continued
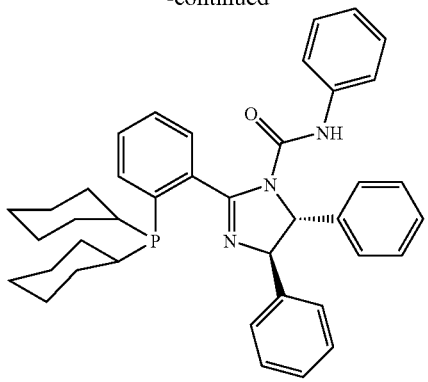
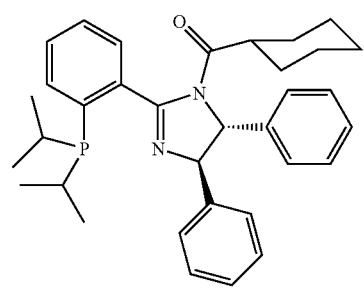
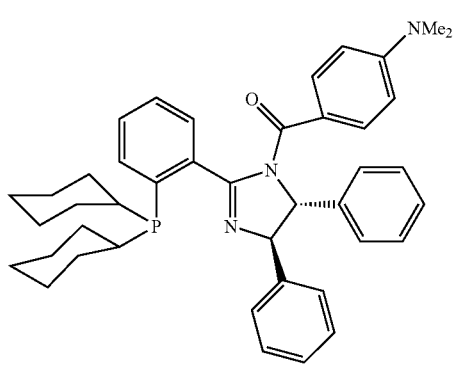
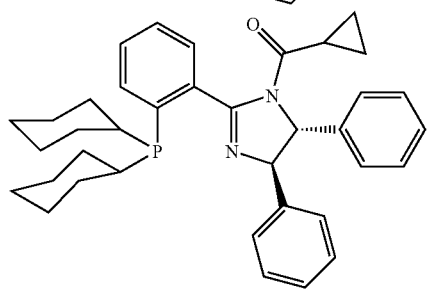
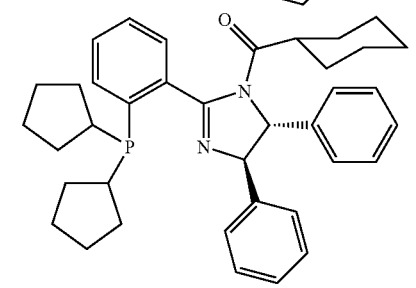
30
-continued
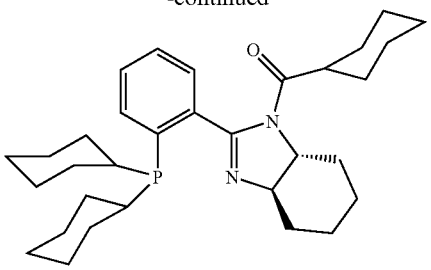
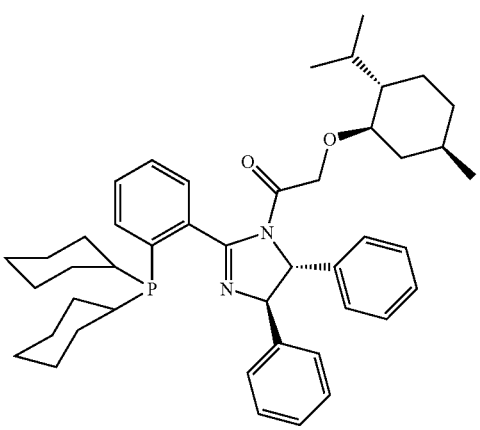
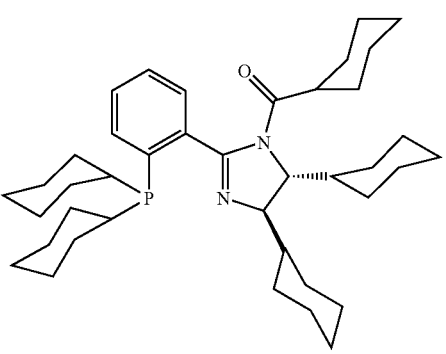
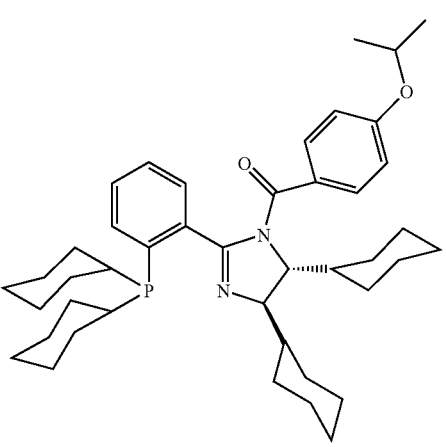

31
-continued
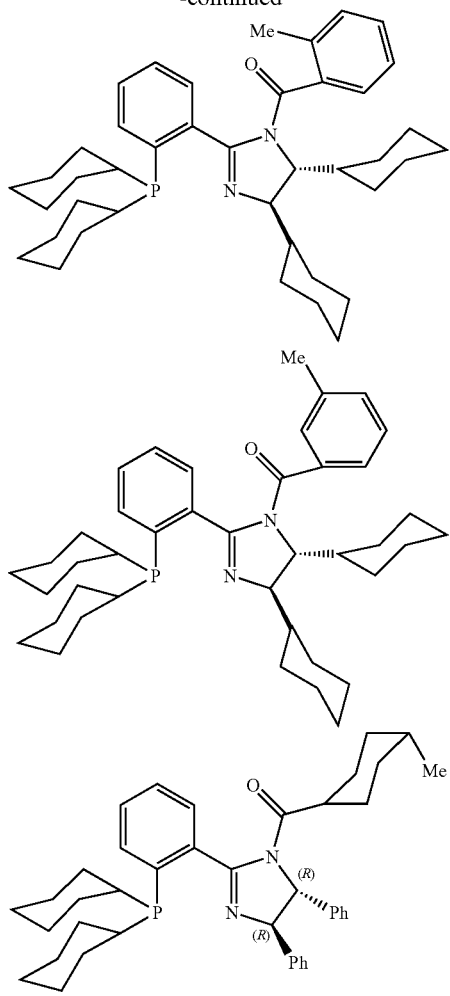
32
-continued
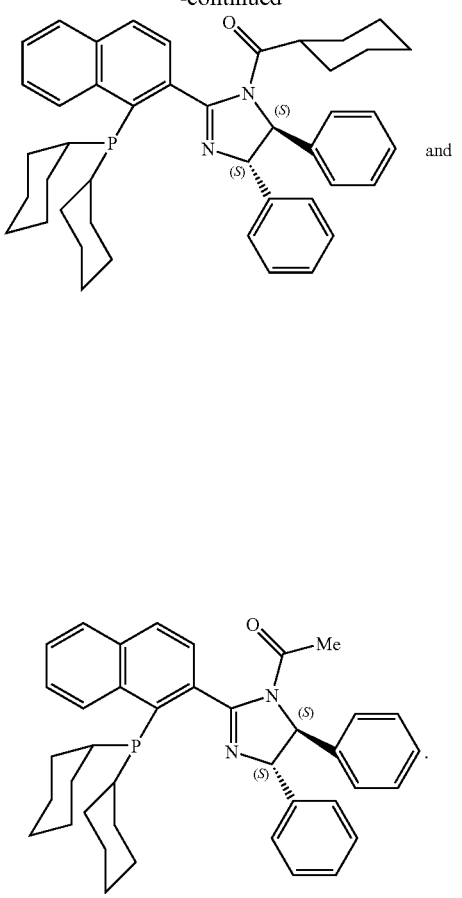
and
* * * * *